United States Patent [19]

Kell

[11] Patent Number: 5,500,372
[45] Date of Patent: Mar. 19, 1996

[54] METHOD OF DETERMINING RENAL CLEARANCES

[75] Inventor: Michael Kell, Atlanta, Ga.

[73] Assignee: Private Clinic Laboratories Inc., Atlanta, Ga.

[21] Appl. No.: 279,400

[22] Filed: Jul. 25, 1994

[51] Int. Cl.$^6$ .................................................. G01N 33/50
[52] U.S. Cl. .................................................. 436/98
[58] Field of Search .............................. 436/63, 98, 174, 436/811

[56] References Cited

U.S. PATENT DOCUMENTS

| | | | |
|---|---|---|---|
| 4,529,708 | 7/1985 | Stephens | 436/98 |
| 4,818,703 | 4/1989 | Pizzolante | 436/98 |

OTHER PUBLICATIONS

Robertshaw, M. "Prediction of Creatinine Clearance from Plasma Creatinine: Comparison of Five Formulae" Br. J. Clin. Pharmac., vol. 28, 275–280 (1989).

Rosano, J. G. et al. "Analytical and Biological Variability of Serum Creatinine and Creatinine Clearance" Clinical Chemistry, vol. 28, 2330–2331 (1982).

Gowans, E. et al. "Biological Variation of Serum and Urine Creatinine and Creatinine Clearance" Chemical Abstracts, vol. 109, No. 35603v, (1988).

Konishi, K. et al. "Prediction of Creatinine Clearance from the Serum Creatinine Clearance", Chemical Abstracts, vol. 102, No. 2885r. (1985).

Primary Examiner—Jeffrey R. Snay
Attorney, Agent, or Firm—Kennedy & Kennedy

[57] ABSTRACT

In a method of determining creatinine clearance for detecting and monitoring renal dysfunction, spot samples of urine and blood from a person are obtained. Specific gravity and creatinine concentration of the urine sample are measured. Creatinine concentration of plasma of the blood sample is also measured. Creatinine clearance is calculated as a function of the measured urine specific gravity, the measured urine creatinine concentration and the measured plasma creatinine concentration.

4 Claims, 2 Drawing Sheets

5,500,372

METHOD OF DETERMINING RENAL CLEARANCES

TECHNICAL FIELD

The present invention relates to methods of detecting and monitoring the progression of renal dysfunction. More particularly, the invention relates to methods of conveniently screening medical patients for occult renal dysfunction.

BACKGROUND OF THE INVENTION

In the fields of medicine and physiology, an accurate assessment of renal function is essential for diagnosis and evaluation of the progression of acute and chronic injuries to the kidneys. During the course of chronic renal disease, the rate of loss of renal function is generally constant. Decreasing function has been shown to occur because of damage to the individual filtration units of each kidney, known as nephrons. Each kidney has approximately $10^6$ nephrons.

In discussing the prognosis and therapy for patients with chronic renal failure (CRF), the residual value of a glomerular filtration rate (GFR) is typically used. The GFR represents the sum total volume of whole blood filtrate which is processed by the glomeruli of both kidneys. For a healthy adult the GFR typically ranges from 120 to 125 ml/min filtered.

Several methods are used to estimate GFR under standard conditions. One method utilizes an intravenous infusion of inulin to measure inulin clearance as an estimate of GFR. The inulin must be carefully regulated to maintain a constant plasma concentration of drug while a timed urine sample is collected, usually over a 24-hour period. Timed urine sample collection is typically inaccurate due to daily variations in urine flow, incomplete emptying of the bladder, and partial loss of the sample. Under optimal conditions, the coefficient of variation (CV) for inulin clearance as compared to GFR is approximately 10 percent in healthy patients and higher in patients with CRF or other severe illnesses.

Another method for estimating GFR employs various radiolabled compounds that are eliminated by glomerular filtration only. Most of these compounds are gamma-emitters, thereby avoiding the error caused by variable quenching in plasma and urine samples as occurs with beta-emitters. While this method is easier to use than the inulin method and has similar CV (10–17 percent), it presents radiation-safety hazards and many practical considerations.

Due to the difficulties inherent in the above methods for estimating GFR, clinicians have relied instead upon measuring creatinine clearances. Creatinine, a waste product of muscle metabolism, is a metabolic side-product occurring in parallel to phosphorocreatine metabolism. Phosphorocreatine is produced from creatine. Creatine is manufactured in the liver from glycine and arginine, transferred to skeletal muscle and converted to the energy-rich compound phosphorocreatine. As creatine cycles between itself and phosphorocreatine in muscle, a small amount of creatine is irreversibly converted to creatinine which is excreted through the kidneys.

The 24-hour creatinine clearance slightly exceeds inulin clearance due to tubular secretion of creatinine in the proximal tubules of each nephron. This method, while not requiring the introduction of an exogenous substance into the patient, does require venipuncture for a blood sample and timed urine sample collection. Consequently, this method is also highly susceptible to errors in timed urine sample collection as discussed above with regard to the inulin clearance method. Estimates for day-to-day variability in ambulatory patients are typically as high as 26 percent. Some portion of this variability is due to daily variations in creatinine metabolism, but the majority is due to urine collection difficulties.

Although estimates for GFR are easier with creatinine than inulin, such procedures are not amenable to routine patient screening due to the necessity of collecting a large volume of urine, usually over a 24 hour period. Consequently, patients are generally only screened for renal function after they develop physical symptoms ascribable to renal dysfunction. This oftentimes allows occult damage to occur that was potentially preventable.

Thus, there exists a need for a simplified method of routinely monitoring patients for renal dysfunction without the necessity for timed urine sample collections and employment of exogenous substances. Accordingly, it is to the provision of such an improved method that the present invention is primarily directed.

SUMMARY OF THE INVENTION

In a preferred form of the invention creatinine clearance is determined for detecting and monitoring renal dysfunction. Spot samples of urine and blood from a person are obtained. Specific gravity and creatinine concentration of the urine sample are measured. Creatinine concentration of plasma of the blood sample is also measured. Creatinine clearance is then calculated as a function of the measured urine specific gravity, the measured urine creatinine concentration and the measured plasma creatinine concentration.

DETAILED DESCRIPTION OF THE INVENTION

Figure 1:
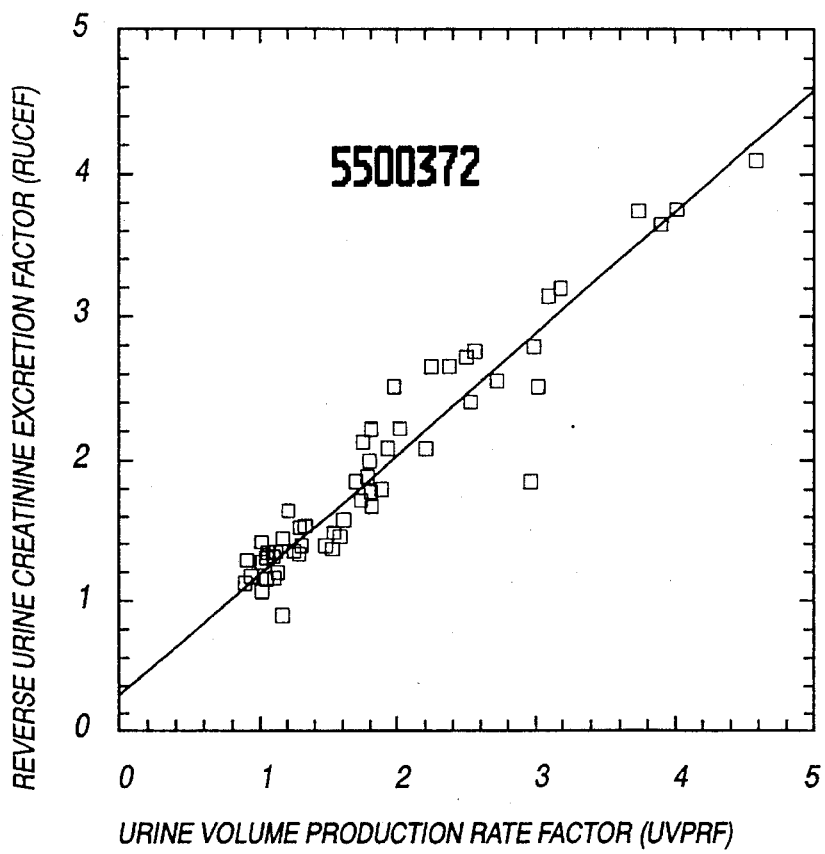
FIG. 1 is a graph of reverse urine creatinine excretion factor (RUCEF) versus urine volume production rate factor (UVPRF) showing their linear relationship.

Glomerular filtration rate is estimated by determining creatinine clearance using a new simplified method which does not require timed urine sample collection. Thus, physicians are now able to detect and monitor renal dysfunction during routine office visits. Spot samples of a person's urine and blood are obtained. The urine specific gravity and the urine and blood plasma creatinine concentrations are determined. A specific gravity normalized creatinine concentration, nu, is calculated by adjusting the urine creatinine concentration for compounding effects of urine specific gravity. A relationship exists between nu and the plasma creatinine concentration such that an approximate value for creatinine clearance is calculated; hence, GFR is estimated.

Collection of Blood and Urine Samples

An aliquot of blood is collected using standard venipuncture techniques, though arterial samples may be used, if necessary. While the time of blood sampling does not have to be concurrent with that of urine sampling, accuracy is enhanced whenever both samples are collected simultaneously or at least within several hours of each other.

The urine sample is collected by simply providing the patient with a standard urine collection bottle into which he or she can urinate. Alternatively, a sample can be collected by catheterization or withdrawn from a urine collection bag. Only several milliliters of urine are required for analysis. With this sampling method, it is not necessary to record the volume collected or completely void the bladder. Loss of a portion of the sample is also not detrimental as long as a sufficient sample remains for analysis. Consequently, this new method overcomes problems long associated with attempts to collect timed urine samples as required by previous clinical methods.

Measurement of Specific Gravity and Creatinine Concentrations

Once a representative urine sample has been obtained, urine specific gravity is measured which typically ranges from 1.004 to 1.035 for normal urine. A Digital Urinometer by Biovation may be used for this test.

Creatinine concentrations for urine and plasma may be determined on many different analyzers, including the REA Creatinine Analysis on the TDX System available from Abbott Laboratories and FARO Analyzers available from Roche Diagnostics. The creatinine concentration in human urine usually ranges from 8 to 500 mg/dl. The range is affected by variables such as age, sex, diet, lifestyle and geographic location. Plasma creatinine concentrations generally are homeostatically maintained by the body at a constant value for each individual patient over his or her lifetime. Daily generation of creatinine remains constant unless crushing injuries or degenerative diseases cause massive muscle damage. Reference values for plasma creatinine concentrations for healthy adult males average between 0.6 to 1.3 mg/dl; for females 0.5 to 1.0 mg/dl. While the illustrative method employs plasma creatinine concentrations, blood or serum creatinine concentrations may also be used.

Determination of the Specific Gravity Normalized Urine Creatinine Concentration

The parameters of a patient's urine, such as pH and specific gravity, vary from one day to the next dependent upon the type and quantities of foods and beverages ingested. Additionally, individuals metabolizes endogenous substances, as well as medications, at different rates. Due to variations in these daily urine parameters, concentration levels for creatinine and other endogenous compounds and drug metabolites can vary over time. Since many endogenous compounds and drugs are weak acids under normal conditions of urine pH, significant tubular resorption does not occur and renal clearance is primarily the result of glomerular filtration. For these compounds, the major variable responsible for observed variations in urine metabolite and drug concentrations is tubular resorption or excretion of free water. The kidneys regulate urine production rates so to maintain normal blood pressure and blood osmolality. This property of the kidneys is indicated by the urine specific gravity, a physical variable relating to urinary solids and urine volume production rate. A mathematical relationship has been discovered to exist between urine creatinine concentrations and urine specific gravity, which herein is given by the specific gravity normalized creatinine concentration, nu.

In order to determine the particular form to use for nu for creatinine or any other compound, it is now realized that renal excretion rates (mg/dl) for drugs and urine metabolites are relatively constant for any patient during a typical day. This constancy has now been experimentally verified by examining the renal excretion rates of methadone, benzodiazepines, other drugs and creatinine and other endogenous metabolites as a function of urine volume production rate. Sequential, complete and timed (1–8 hours holding periods) aliquots of urine for 12 compliant control subjects were collected over 24 to 72 hour periods. For each urine aliquot, urine volume production rate (ml/min), specific gravity and creatinine concentration (mg/dl) were determined. Using this data, a dimensionless, linear relationship was found to exist, that is the same for all patients, between a urine volume production rate factor (UVPRF) and a reverse urine creatinine excretion factor (RUCEF). For each individual, control, urine collection period, the UVPRF is defined by the ratio of urine volume production rate for each urine aliquot collected, v, to the urine volume production rate for the most concentrated sample in the collection period with a specific gravity usually near 1.030, v', $$UVPRF = v/v'. \quad (1)$$

The RUCEF factor is defined by the ratio of the creatinine concentration of the most concentrated urine aliquot with a specific gravity usually near 1.030, u', to the creatinine concentration for each urine aliquot collected, u, $$RUCEF = u'/u. \quad (2)$$

This linear relationship is shown in FIG. 1. The best fit linear regression line is given by the expression, $$RUCEF = 0.942 \cdot UVPRF + 0.121 \quad (3)$$

$$u'/u = 0.942 \cdot v/v' + 0.121 \quad (4)$$

where statistical evaluation results in an adjusted squared multiple R=0.985, a standard error of the estimate= 0.242, and a F-ratio=4965.

Therefore, contrary to the traditional teachings of those skilled in the art, urine drug and metabolite concentrations, u, are inversely related to the volume of urine produced by the kidneys, v, clearly demonstrating that the product (u·v) is constant at any particular time point and urine pH.

Since (u·v) at any time is a constant, steady-state value, it follows that from Equation (4) some empirical mathematical relationship must exist between u and v such that given an arbitrary urine volume production rate v' and an equivalent u' at a reference point (specific gravity 1.030):

$$\{u \cdot v\}_{sg\ actual} = \{u' \cdot v'\}_{sg\ 1.030} \quad (5)$$

or upon rearrangement for u' gives, $$u' = u \cdot (v/v') \quad (6)$$

where the products given in Equation (6) are those measured for a spot urine collected with an actual specific gravity and a corrected specific gravity typical of a morning void of 1.030.

Figure 2:
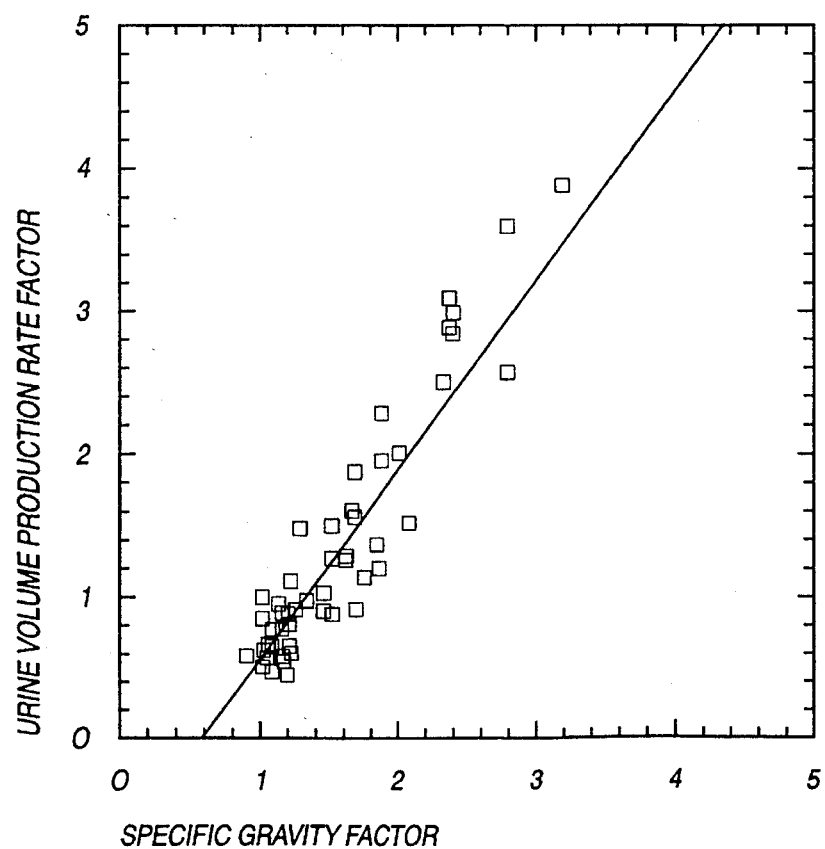
FIG. 2 is a graph of urine volume production rate factor (UVPRF) versus specific gravity factor (SGF) showing their linear relationship.

Using controlled urine collections, a urine volume production rate v' of 0.44 ml/min for persons with reasonably normal renal functions at a specific gravity of 1.030 was measured. It was discovered that a linear relationship exists between the urine volume production rate factor and the specific gravity factor (SGF), {(1.030− 1.000)/(sg−1.000)}, as shown in FIG. 2 and given as follows:

$$UVPRF = v/v' = 2.43 \cdot SGF - 1.43 \tag{7}$$

where the adjusted squared multiple R=0.856, standard error of the estimate=0.787, F-ratio 482.

Substituting Equation (7) into Equation (6) the specific gravity normalized creatinine concentration, nu, is calculated by adjusting the actual urine creatinine concentration, u, for compounding effects of urine specific gravity.

$$nu = u' = u \cdot (v/v') = u \cdot [2.43 \cdot SGF - 1.43] \tag{8}$$

Calculation of Creatinine Clearance

The creatinine clearance is calculated by estimating three variables, the plasma creatinine concentration, the urine creatinine concentration and the volume of urine collected over a 24 hour collection period. Creatinine clearance is calculated utilizing the standard dimensionally correct relationship known as the renal clearance formula, which is:

$$cl = (u \cdot v)/p \tag{9}$$

where cl is renal clearance (ml/min), u is actual urine concentration (mg/dl), v is the volume of urine collected in time (ml/min) or otherwise known as the urine volume production rate, and p is the measured plasma concentration at the midpoint of the collection period (mg/dl). The plasma and actual urine creatinine concentrations are measurable as discussed above by using known chemical or other methods. However, under normal clinical screening situations the actual value of the urine volume production rate, v, is not available to physicians due to the great effort and expense required to obtain this value by collecting a timed urine sample for ambulatory patients during normal health check-ups.

By substituting Equations (5) and (8) into the renal clearance formula of Equation (9), the creatinine clearance is calculated in accordance with the invention as follows:

$$\begin{aligned} cl &= (v \cdot u)/p \\ &= (v' \cdot u')/p \\ &= v' \cdot u \cdot [2.43 \cdot SGF - 1.43]/p \end{aligned} \tag{10}$$

All the values of Equation (10) are readily available, v' is equal to 0.44 ml/min and u, p and urine specific gravity are obtainable using standard measurement techniques. The problem of obtaining urine volume production rate is now eliminated since a spot urine sample may now be collected rather than a timed urine sample in order to estimate GFR. There is no additional inconvenience for the patient since urine samples are often collected from patients for other reasons. Moreover, by evaluating sequential samples from an individual patient an accurate individual base value of creatinine clearance and GFR is obtained.

Biological Variation in Plasma/Urine Creatinine Concentrations

Based upon past literature references, some degree of biological variability was to be expected in repetitive measurements of urine and plasma creatinine concentrations. However, quantitative data actually available demonstrating variability was minimal. Thus, data relating to creatinine concentration variability was developed.

To evaluate daily variation in plasma creatinine concentration, morning and afternoon blood samples were drawn for 13 control subjects. Actual before noon (AM) and after noon (PM) plasma creatinine concentrations measured for each subject are shown in Table A, as well as the PM/AM ratio. Using the ratio data, the mean ratio was 1.02, a standard deviation (SD) of 0.12 and a CV of 11.6%. A slightly elevated ratio was to be expected since plasma creatinine concentration is known to increase slightly with the ingestion of protein and with exercise.

TABLE A

Daily Variation in Plasma Creatinine

| Subject | AM Creatinine (mg/dl) | PM Creatinine (mg/dl) | PM/AM Creatinine Ratio |
|---|---|---|---|
| A | 1.11 | 1.18 | 1.063 |
| B | 1.14 | 1.17 | 1.114 |
| C | 1.27 | 1.06 | 0.835 |
| D | 0.81 | 0.67 | 0.827 |
| E | 1.4 | 1.53 | 1.093 |
| F | 0.91 | 1.06 | 1.165 |
| G | 0.85 | 1.01 | 1.188 |
| H | 1.30 | 1.27 | 0.977 |
| I | 1.34 | 1.45 | 1.082 |
| J | 0.90 | 0.79 | 0.878 |
| K | 1.20 | 1.25 | 1.042 |
| L | 1.20 | 1.23 | 1.025 |
| M | 1.20 | 1.15 | 0.958 |
| Mean | | | 1.02 |
| SD | | | 0.12 |

Figure 3:
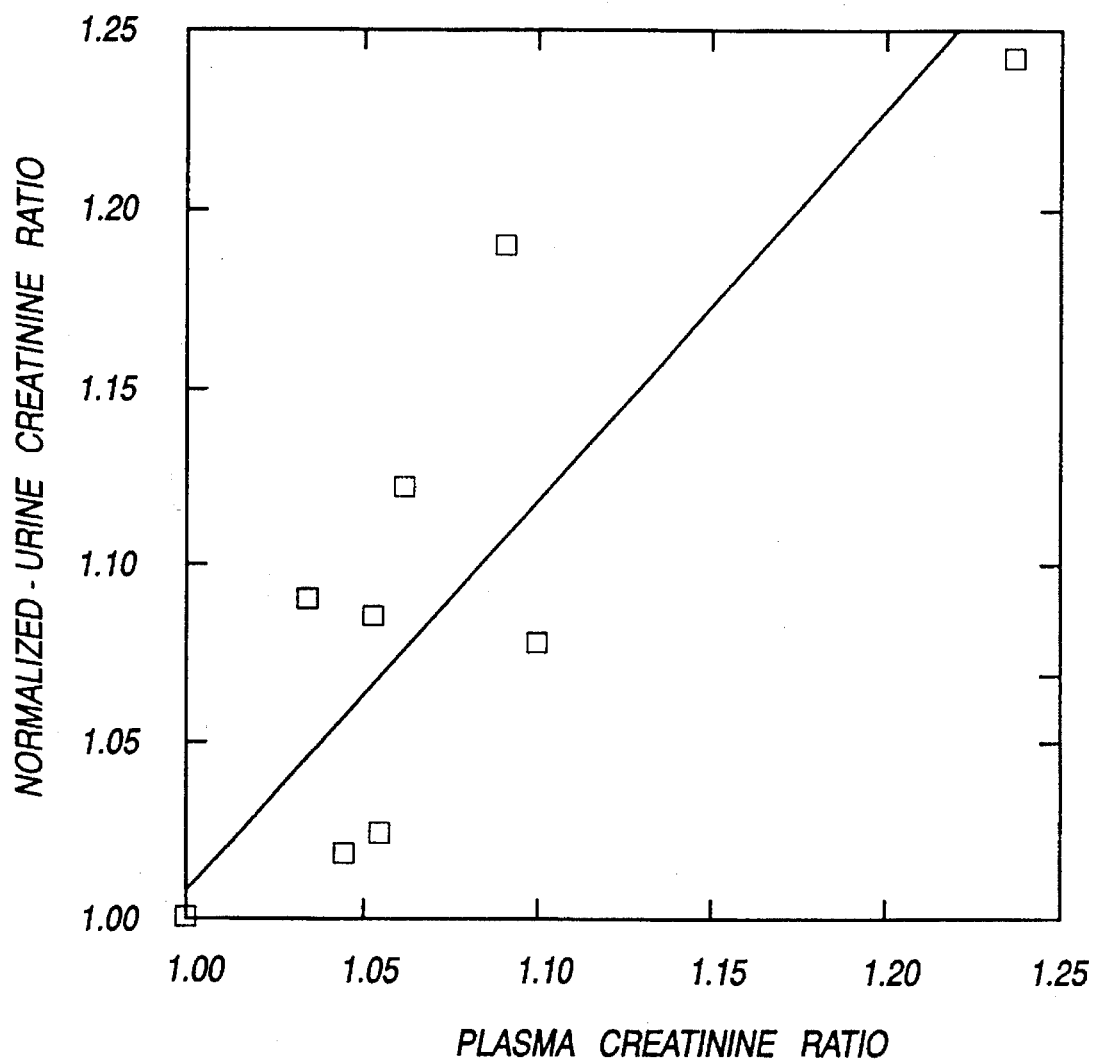
FIG. 3 is a graph of normalized-urine creatinine ratio versus plasma creatinine ratio showing their linear relationship.

The possible effects of this daily variation in plasma creatinine concentration was explored. Simultaneous AM and PM measurements of plasma and urine creatinine concentrations were made in several subjects. Taking the lowest plasma creatinine concentration as the plasma reference and the corresponding specific gravity normalized urine creatinine concentration as the urine reference, ratios of the form $X/X_{Ref}$ were calculated. FIG. 3 displays data for nine subjects plotted as plasma creatinine ratio versus specific gravity normalized urine creatinine ratio. Inspection of this curve indicates that specific gravity normalized urine creatinine concentration is essentially linearly related to plasma creatinine concentration. Thus, small daily variations in plasma creatinine concentrations are accurately related in the urine such that creatinine clearance remains virtually constant.

Day-to-day variability for specific gravity normalized urine creatinine concentration were followed in a patient cohort using once or twice a week urine testing. Analysis of this data demonstrated a mean CV of 15.5% with a standard deviation of 4.4%. Based upon these results, the slight amounts of biological variability seen for plasma creatinine concentration is not expected to significantly effect the utilization of this new method.

Standard vs. Proposed Estimates for Creatinine Clearance

Comparative data demonstrating acceptable agreement between conventional clinical estimates of creatinine clearance and those of the present invention was generated. Each subject was asked to measure and record the amount and time of each urine void. Specific gravity and urine and plasma creatinine concentrations were measured for each subject. Using this data, creatinine clearances were calculated using Equation (10). Shown in Table B is detailed collection data for a single subject with a plasma creatinine concentration of approximately 1.29 mg/dl. Shown in Table C is summary data for six subjects.

TABLE B

Creatinine Clearance Comparison of Conventional and Proposed Methods

| Sample | Spec Grav | Act Uri Cr conc,u (mg/dl) | Nor Uri Cr conc, nu (mg/dl) | Uri Vol (ml/min) | Std. Cr Clear (ml/min)[a] | Calc. Cr Clear (ml/min)[a] |
|---|---|---|---|---|---|---|
| 1 | 1.020 | 144 | 319 | **** | **** | 108.0 |
| 2 | 1.022 | 167 | 315 | 0.83 | 106.6 | 106.5 |
| 3 | 1.024 | 219 | 352 | 0.60 | 101.1 | 119.2 |
| 4 | 1.015 | 69 | 237 | 1.17 | 62.1 | 80.1 |
| 5 | 1.009 | 40 | 266 | 2.33 | 71.7 | 90.3 |
| 6 | 1.015 | 110 | 377 | 0.98 | 82.9 | 127.7 |
| 7 | 1.019 | 117 | 282 | 1.05 | 94.5 | 95.3 |
| 8 | 1.024 | 180 | 267 | 0.70 | 96.9 | 97.9 |
| 9 | 1.025 | 240 | 289 | 0.54 | 99.7 | 97.8 |
| 10 | 1.022 | 143 | 269 | 0.94 | 103.4 | 91.2 |
| 11 | 1.015 | 64 | 219 | 2.03 | 99.9 | 74.1 |
| Mean | | 135.7 | 290.2 | | 91.9 | 99.0 |
| SD | **** | 63.7 | 47.3 | **** | 14.8 | 16.6 |
| CV (%) | | 44.6 | 16.8 | | 16.1 | 16.8 |

TABLE C

Summary Creatinine Clearance Data

| Subject | No. Urine Samples | Std. Cr Clearance (ml/min)[a] | Calc. Cr Clearance (ml/min)[a] |
|---|---|---|---|
| A | 5 | 87.0 (SD 6.9) | 96.7 (SD 7.4) |
| B | 5 | 91.2 (SD 4.4) | 86.9 (SD 10.1) |
| C | 7 | 111.0 (SD 11.6) | 105.3 (SD 11.4) |
| D | 7 | 92.0 (SD 11.1) | 81.5 (SD 8.4) |
| E | 7 | 89.9 (SD 8.7) | 84.3 (SD 12.0) |
| F | 11 | 91.9 (SD 14.8) | 99.0 (SD 16.6) |

SUMMARY

It is thus seen that a method is now provided for monitoring creatinine clearance in ambulatory and hospitalized patients using spot urine samples rather than timed urine sample collection. The method utilizes readily obtainable urine creatinine concentrations from evaluation of patient urine samples to determine specific gravity normalized urine creatinine concentrations. All can be compared to historical patient data to follow trends in renal GFR. The invention is clinically practical without high laboratory cost or the need to collect timed urine samples or use exogenous markers.

While this new method has been described in detail with particular references to the preferred embodiment thereof, it should be understood that many modifications, additions and deletions may be made thereto without departure from the spirit and scope of the inventive method as set forth in the following claims.

I claim:

1. A method of determining creatinine clearance for detecting and monitoring renal dysfunction comprising the steps of:

(a) obtaining spot samples of urine and blood from a person;

(b) measuring specific gravity and creatinine concentration of the urine sample;

(c) measuring creatinine concentration of plasma of the blood sample; and (d) calculating creatinine clearance as a function of the measured urine specific gravity, the measured urine creatinine concentration and the measured plasma creatinine concentration.

2. The method of claim 1 wherein step (d) the creatinine clearance is calculated in accordance with the equation $$cl = v' \cdot u \cdot (k_1 \cdot SGF - k_2)/p$$

wherein cl is the creatinine clearance, v' is the urine volume production rate for persons with reasonably normal renal functions, u is the measured urine creatinine concentration, SGF is the specific gravity factor, p is the measured plasma creatinine concentration, and $k_1$ and $k_2$ are constants.

3. The method of claim 2 wherein $k_1$ is equal to 2.43 and $k_2$ is equal to 1.43.

4. A method of determining creatinine clearance for detecting and monitoring renal dysfunction comprising the steps of:

(a) obtaining spot samples of urine and blood from a person;

(b) measuring the specific gravity and creatinine concentration of the urine sample;

(c) measuring the creatinine concentration of serum of the blood sample; and (d) calculating creatinine clearance as a function of the measured urine specific gravity, the measured urine creatinine concentration and the measured serum creatinine concentration.

* * * * *